United States Patent [19]

Tiffany et al.

[11] Patent Number: 4,731,081
[45] Date of Patent: Mar. 15, 1988

[54] RUPTURE-RESISTANT PROSTHESIS WITH CREASABLE SHELL AND METHOD OF FORMING SAME

[75] Inventors: John S. Tiffany, Ventura; R. Alastair Winn, Santa Barbara, both of Calif.

[73] Assignee: Mentor Corporation, Goleta, Calif.

[21] Appl. No.: 778,158

[22] Filed: Sep. 17, 1985

Related U.S. Application Data

[63] Continuation of Ser. No. 649,954, Sep. 11, 1984, abandoned, which is a continuation of Ser. No. 350,916, Feb. 22, 1982, abandoned.

[51] Int. Cl.⁴ ............................................. A61F 2/12
[52] U.S. Cl. ........................................................ 623/8
[58] Field of Search ................ 623/7, 8, 11; 128/1 R, 128/DIG. 22

[56] References Cited

U.S. PATENT DOCUMENTS

| | | | |
|---|---|---|---|
| 2,542,619 | 2/1951 | Bernhardt | 623/7 |
| 2,636,182 | 4/1953 | Freedman | 3/36 |
| 3,883,902 | 5/1975 | Lynch | 3/36 |
| 3,986,213 | 10/1976 | Lynch | 3/36 |
| 4,138,382 | 2/1979 | Polmanteer | 3/36 X |

Primary Examiner—Richard J. Apley
Assistant Examiner—David J. Isabella
Attorney, Agent, or Firm—Kinney & Lange

[57] ABSTRACT

A surgically implantable prosthesis, such as a mammary implant, that is rendered rupture-resistant by injecting a liquid with uniformly dispersed lubricating material into a flexible creasable shell during manufacture or surgical implantation. The lubricating material, such as polyvinylpyrrolidone, polyvinyl alcohol, hydroxyethyl starch, or lecithin is uniformly dispersed in a carrier inflating liquid such as normal saline. The lubricating material reduces frictional wear along opposed inner surfaces during sliding contact in a creased area in the shell wall after surgical implantation.

6 Claims, 6 Drawing Figures

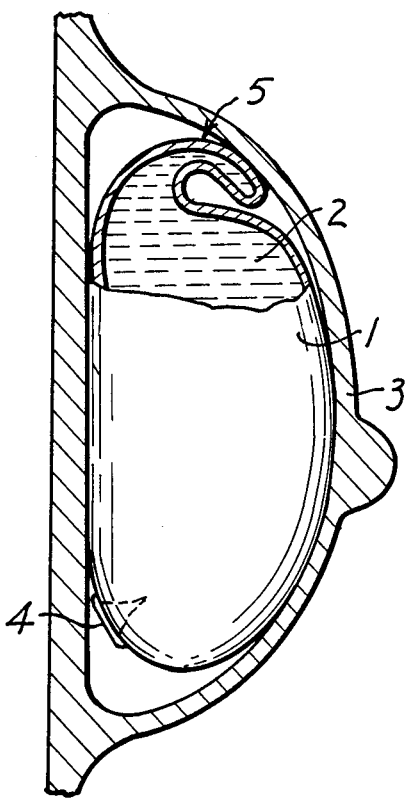
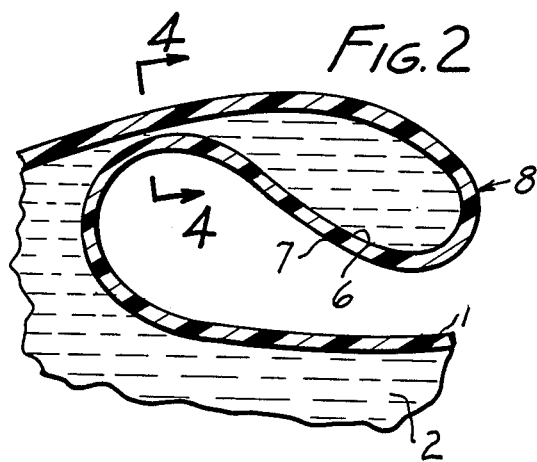
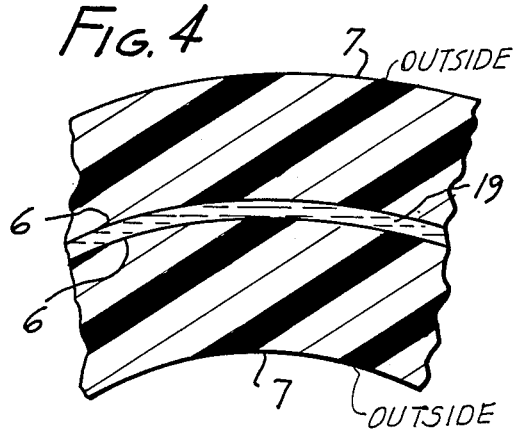
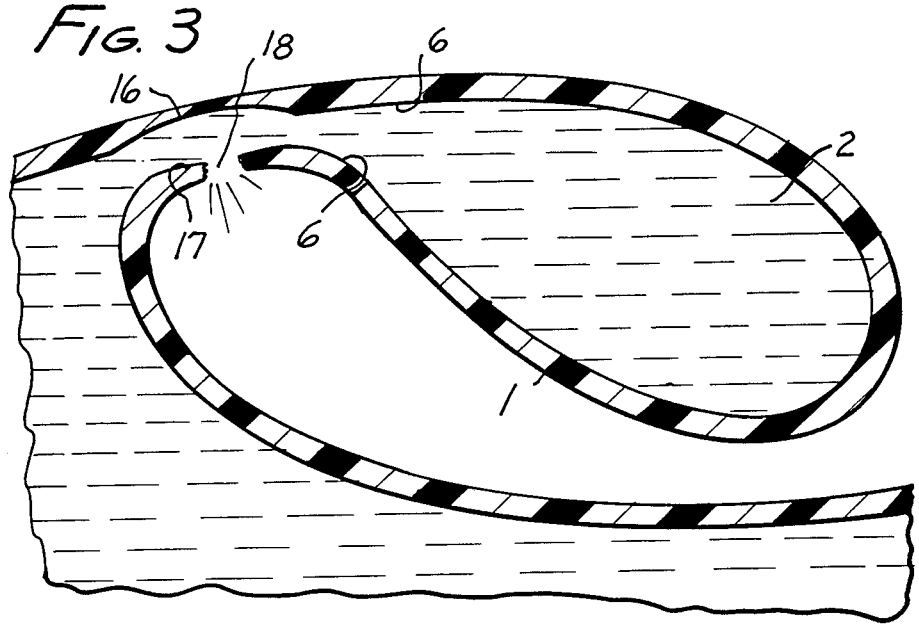

RUPTURE-RESISTANT PROSTHESIS WITH CREASABLE SHELL AND METHOD OF FORMING SAME

REFERENCE TO CO-PENDING APPLICATION

This application is a continuation of pending application Ser. No. 06/649,954 filed Sept. 11, 1984, abandoned as of the filing date of the present application, which was a continuation of application Ser. No. 06/350,916 filed Feb. 22, 1982, abandoned on Sept. 11, 1984.

BACKGROUND OF THE INVENTION

Surgically implanted flexible bag-type mammary prostheses have suffered a serious problem with the bag rupturing in certain cases after surgical implantation. This is believed to occur more frequently when the bag develops a crease. Several theories have been advanced to explain just why such a bag ruptures. Some believe it is due to the stress differential between inner and outer surfaces of a bag wall section and a crease area caused by one wall surface being in compression and the other being in tension. Others believe that this is caused by a change in the physical properties such as modulus, etc., over a prolonged period of maintaining a crease. Still others believe that the bag failures to be caused at least in part by friction between opposing wall sections in a fold area. This latter view is explained in Rees et al. in "The Use of Inflatable Breast Implants," *Plastic and Reconstructive Surgery*, Volume 52, Number 6, December 1973, pp. 609–615.

This type of bag wall failure in a creased area has been known for many years as "fold flaw." All of the mechanisms explained above may contribute in causing fold flaw failure. Heretofore, a solution to reduce fold flaw failure has not existed.

SUMMARY OF THE INVENTION

The present invention overcomes these difficulties with the unexpected discovery and analysis of the dominating mechanism of perhaps many contributing causes for fold flaw failure and provides a solution to substantially reduce fold flaw failure. This invention involves inflating either during manufacture or surgical implantation a flexible, creasable sheel of a prosthesis with an inflating liquid, such as normal saline, which has uniformly dispersed in such liquid a separate lubricating material. This lubricating material is preferably a hydrophilic polymer or surface active agent, such as polyvinylpyrrolidone, polyvinyl alcohol, hydroxyethyl starch, lecithin, fatty acid salts, fatty acid esters, which is bioabsorbable and does not separate or settle out from its carrier liquid. Other non-aqueous bioabsorbable material such as cottonseed oil, and peanut oil, could also be used. The lubricating material reduces the abrasive damage between two sliding inner surfaces of the bag wall at a crease that occurs after or during surgical implantation.

BRIEF DESCRIPTION OF THE DRAWINGS

FIG. 1 is a schematic sectional view of a human breast which has been surgically implanted with a mammary prosthesis that has developed a fold;

FIG. 2 is an enlarged fragmentary view in section of the fold flaw area of the prosthesis of FIG. 1 prior to rupture;

FIG. 3 is still further enlarged view similar to FIG. 2, but showing the prosthesis after rupture;

FIG. 4 is an enlarged fragmentary sectional view taken along 4—4 of FIG. 2;

DETAILED DESCRIPTION OF THE PREFERRED EMBODIMNT

Figure 5:
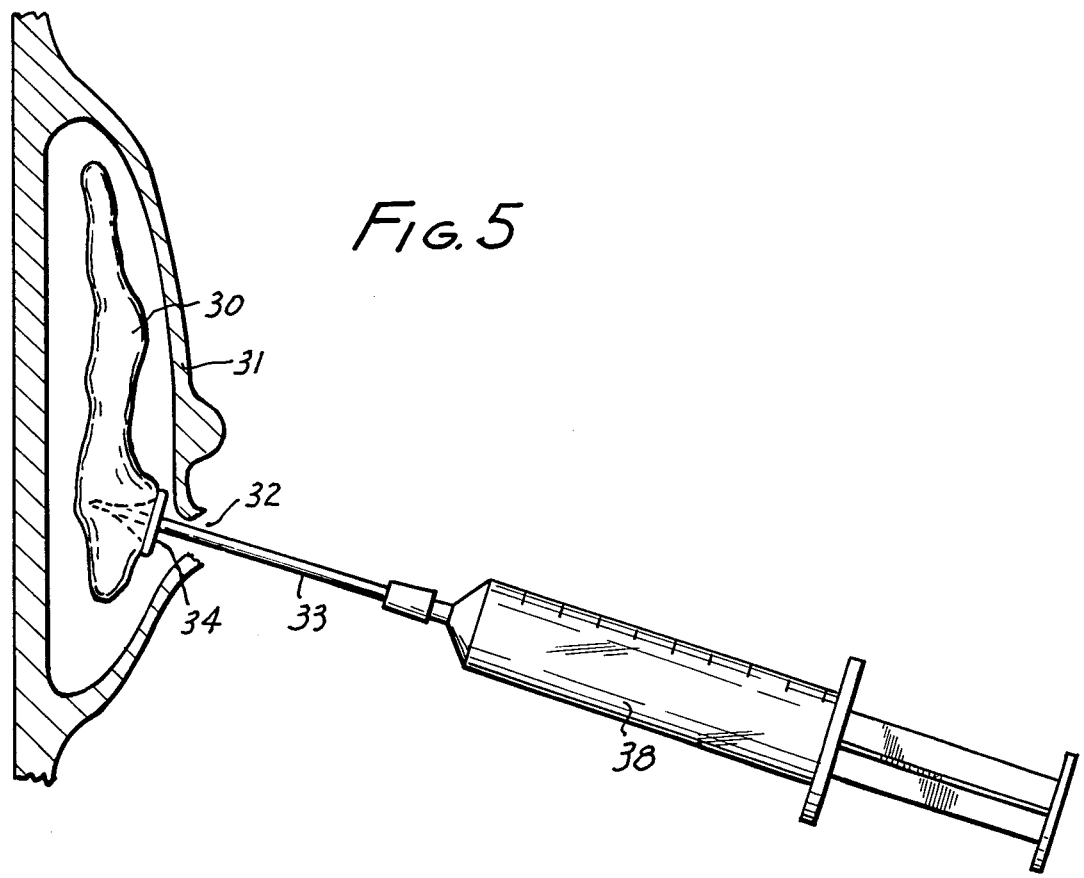
FIG. 5 is a view of a mammary implant to be inflated during surgery.

In FIG. 1, the mammary prosthesis which includes a flexible, creasable shell 1 with an inflating liquid 2 has been surgically implanted within a breast 3 of a patient. A filling valve 4 is schematically shown at a rear of the prosthesis. At an upper portion of the prosthesis is shown a creased area, shown generally at 5. As explained above, this has been known for years as the "fold flaw" problem because the shell 1 tends to rupture at this folded area, perhaps many months or years after surgical implantation.

As shown in the enlarged view of FIG. 2, the prosthesis with wall 1, sometimes known as the "bag" has an inner surface 6 and an outer surface 7. One theory of fold flaw failure was that the outer surface 7 being in tension and inner surface being in compression in the loop or bight area, shown generally at 8, caused fatigue, creep or change in overall modulus, etc. of the wall material itself.

Applicants have discovered that among perhaps many contributing factors, abrasion between two adjacent wall surfaces in the fold area is dominant. As shown in FIG. 3, opposing portions of the inner surface 6 of the back wall 1 have abraded a thin area 16 from an inner surface 6 of the bag wall. At opposing inner wall surface 17 opposing wall portion 16 has abraded completely through forming rupture 18 which permits the liquid to drain from the bag. This is a disadvantage because the mammary implant loses its structural shape within the breast. It is also undesirable to have the inflating liquid, such as normal saline, in direct contact with the breast tissue where it can shift, be biologically absorbed, etc.

In the enlarged sectional view of FIG. 4, two portions of the inner surface 6 of the bag are in very close proximity to each other. As the patient moves or exercises, these surfaces 6 shift relative to each other and can cause the abrasion rupture of FIG. 3. Although some of the liquid 2 may migrate into the abrasion area and temporarily separate the two abrasion areas, inflating liquid of normal saline has not effectively controlled the fold flaw failure that has been known for many years. The applicants have unexpectedly found that by dispersing or dissolving a separate lubricating material in the inflating liquid (normal saline), fold flaw failure under simulated surgical implantation has been substantially reduced or eliminated. This is believed to be caused by lubricating or wetting action which reduces friction between the opposed portions of the inner surface of the bag wall. As shown in FIG. 4, the lubricating solution, suspension, colloid, or emulsion would be in the small space 19.

The lubricating material is preferably a solution or suspension of hydrophilic polymer material, such as polyvinylpyrrolidone, polyvinyl alcohol, hydroxyethyl starch, and lecithin, which are biocompatible and can be added to the inflating liquid carrier. Wetting agents and surfactants such as fatty acid salts or esters, further provide the desired lubricating action. We have found that the lubricating material works very well when it constitutes less than 70% by weight of the total inflating liquid (including lubricating material) that is injected into the flexible bag. Preferably the lubricating material constitutes from about 5% to 10% by weight. Excellent results have been obtained by using polyvinylpyrrolidone within this range. Other non-aqueous bio-absorbable fill material such as cottonseed oil, or peanut oil, will also provide the desired lubricating action.

Alternatively, solids in their pure form such as the polyvinylpyrrolidone, polyvinyl alcohol, or hydroxyethyl starch can be placed in the prosthesis during manufacturing, so that the surgeon or hospital personnel need only inject isotonic saline therein to effect inflation.

FIG. 5 shows a method of forming the rupture-resistant mammary prosthesis during surgery. Here a deflated bag 30 is surgically implanted into a breast 31 through a surgical opening 32. A catheter 33 is inserted through an inflation valve 34. Catheter 33 has already been connected through a syringe or other inflating device 38 containing the inflation liquid which has uniformly dispersed lubricating material. After the bag 30 has been inflated with the liquid, valve 34 is sealed and catheter 33 removed. Finally the surgical wound is closed. This process works very well when the inflating liquid is normal saline containing lubricating material. Alternately, as described above, normal saline may be added to the prosthesis containing the dry form of the lubricant.

Figure 6:
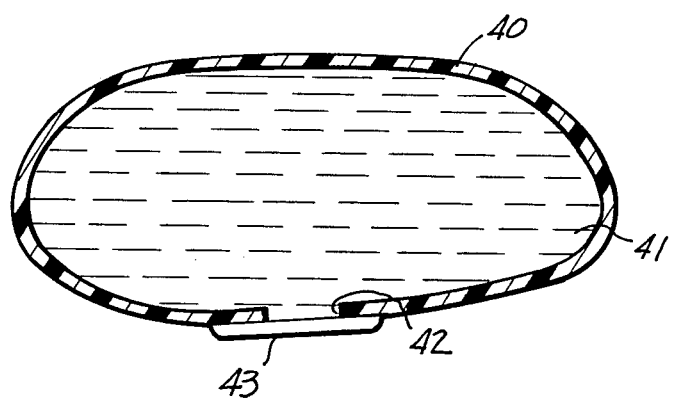
FIG. 6 is a sectional view of a mammary implant which has been pre-inflated by a manufacturer.

An alternate method of forming a rupture-resistant prosthesis includes the flexible bag 40 shown in FIG. 6 which includes an inflating liquid 41 that was previously injected through an opening 42 by manufacturer. Opening 42 was sealed by a patch 43 prior to surgical implantation. A pre-filled mammary is implanted through a surgical opening in the breast and then the surgical opening is closed. It is understood that the inflation liquid can be either a single bag type prosthesis, or a double bag type, such as in the Hartley U.S. Pat. No. 3,934,274.

In the foregoing description, specific examples have been used to illustrate the invention. However, it is understood by those skilled in the art that modifications can be made thereto without departing from the spirit and scope of the invention.

We claim:

1. An implantable rupture-resistant inflatable mammary prosthesis comprising:
    a flexible, biocompatible, inflatable shell; and
    a biocompatible inflating fluid occupying effectively the entire interior space, said inflating fluid further comprising saline and an aqueous liquid carrier having a separate lubricating material uniformly dispersed therein, the lubricating material selected from the group consisting of polyvinylpyrrolidine, polyvinyl alcohol, hydroxyethyl starch, lecithin, peanut oil, cottonseed oil, fatty acid salts and fatty acid esters, wherein the lubricating material is less than 70% by weight of the inflating fluid.

2. A rupture-resistant prosthesis as set forth in claim 1, wherein the lubricating material comprises from about 5% to about 10% by weight of the inflating fluid.

3. An implantable rupture-resistant inflatable breast prosthesis comprising:
    an unfilled inflatable flexible biocompatible shell which has a wall with inner and outer surfaces, said wall defining an inflatable interior space confined within said inner surface; and
    a separate container disposed within said interior space, said container filled with a biocompatible inflating liquid in an amount sufficient to fill effectively the entire interior space of said shell, said inflating liquid further comprising an aqueous liquid carrier and a lubricating agent, the lubricating material selected from the group consisting of polyvinylpyrrolidine, polyvinyl alcohol, hydroxyethyl starch, lecithin, peanut oil, cottonseed oil, fatty acid salts and fatty acid esters, said lubricating agent being less than about 70% by weight of the inflating liquid uniformly dispersed in said inflating liquid for reducing self-abrasion damage to the inner surface portions of the shell wall when said inflating liquid is transferred from the container and confined within the shell.

4. A method of forming a rupture-resistant prosthesis having a flexible, implantable, inflatable biocompatible shell comprising the steps of:
    a. injecting a biocompatible inflating liquid into the shell to inflate said shell with a lubricating material uniformly therein, the lubricating material selected from the group consisting of polyvinylpyrrolidine, polyvinyl alcohol, hydroxyethyl starch, lecithin, peanut oil, cottonseed oil, fatty acid salts and fatty esters, with the lubricating material being less than 70% by weight of the inflating liquid; and
    b. sealing the shell.

5. The method of claim 4 wherein the lubricating material is from about 5% to 10% by weight of the inflating liquid.

6. A method of forming a rupture-resistant prosthesis comprising:
    providing a flexible, implantable, inflatable biocompatible shell containing solid biocompatible lubricating agents selected from the group consisting of polyvinylpyrrolidine, polyvinyl alcohol and hydroxyethyl starch, in a quantity such that the lubricating agent will be less than 70% by weight of an inflating biocompatible fluid within the shell;
    injecting said biocompatible inflating fluid into the shell; and
    sealing the shell.

* * * * *

UNITED STATES PATENT AND TRADEMARK OFFICE
CERTIFICATE OF CORRECTION

PATENT NO. : 4,731,081
DATED : 03/15/88
INVENTOR(S) : TIFFANY, ET AL.

It is certified that error in the above-identified patent and that said Letters Patent is hereby corrected as shown below:

In Col. 3, Line 56, please delete the word "polyvinylpyrrolidine" and insert in lieu thereof --polyvinylpyrrolidone--.

In Col. 4, Line 20, please delete the word "polyvinylpyrrolidine" and insert in lieu thereof --polyvinylpyrrolidone--.

In Col. 4, Line 35, please delete the word "polyvinylpyrrolidine" and insert in lieu thereof --polyvinylpyrrolidone--.

In Col. 4, Line 50, please delete the word "polyvinylpyrrolidine" and insert in lieu thereof --polyvinylpyrrolidone--.

Signed and Sealed this

Twenty-fifth Day of August, 1992

Attest:

DOUGLAS B. COMER

*Attesting Officer*  *Acting Commissioner of Patents and Trademarks*